United States Patent
Goldfarb et al.

(10) Patent No.: US 10,016,290 B2
(45) Date of Patent: Jul. 10, 2018

(54) WALKING CONTROLLER FOR POWERED ANKLE PROSTHESES

(71) Applicant: VANDERBILT UNIVERSITY, Nashville, TN (US)

(72) Inventors: Michael Goldfarb, Franklin, TN (US); Amanda Huff Shultz, Hickory, TN (US); Brian E. Lawson, Nashville, TN (US); Jason E. Mitchell, Greenbrier, TN (US); Don Truex, Mufreesboro, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 14/428,058

(22) PCT Filed: Sep. 17, 2013

(86) PCT No.: PCT/US2013/060110
§ 371 (c)(1),
(2) Date: Mar. 13, 2015

(87) PCT Pub. No.: WO2014/043681
PCT Pub. Date: Mar. 20, 2014

(65) Prior Publication Data
US 2015/0297364 A1    Oct. 22, 2015

Related U.S. Application Data

(60) Provisional application No. 61/701,779, filed on Sep. 17, 2012.

(51) Int. Cl.
*A61F 2/66* (2006.01)
*A61F 2/70* (2006.01)
(Continued)

(52) U.S. Cl.
CPC .............. *A61F 2/6607* (2013.01); *A61F 2/66* (2013.01); *A61F 2/68* (2013.01); *A61F 2/70* (2013.01);
(Continued)

(58) Field of Classification Search
None
See application file for complete search history.

(56) References Cited

U.S. PATENT DOCUMENTS

| | | | |
|---|---|---|---|
| 4,209,860 A | 7/1980 | Graupe | |
| 4,685,925 A | 8/1987 | Childress et al. | |

(Continued)

FOREIGN PATENT DOCUMENTS

| | | |
|---|---|---|
| WO | WO 2010027968 A2 | 3/2010 |
| WO | WO 2011026086 A1 | 3/2011 |
| WO | WO 2011096965 A2 | 8/2011 |

OTHER PUBLICATIONS

International Search Report dated Apr. 23, 2014 in PCT/US2013/060110.

(Continued)

*Primary Examiner* — David H Willse
(74) *Attorney, Agent, or Firm* — Nixon Peabody LLP; Eduardo J. Quinones

(57) ABSTRACT

Described herein are systems and methods for a powered ankle/foot prosthesis and controller that utilizes piecewise emulated passive impedances to provide for walking at various cadences and on various slopes and for ground slope adaptive standing. A powered prosthesis using these systems and methods is capable of emulating any physical behavior provided by the healthy joint, and additionally describes a control system that utilizes the sensing and actuation system on the prosthesis to provide appropriate ankle joint impedances. Further, the control system incorporates a finite-state- (Continued)

based structure, and within each state, emulates the behavior of the healthy joint with strictly passive impedance functions.

22 Claims, 10 Drawing Sheets

(51) Int. Cl.
  *G05B 15/02* (2006.01)
  *A61F 2/50* (2006.01)
  *A61F 2/76* (2006.01)
  *A61F 2/68* (2006.01)
(52) U.S. Cl.
  CPC ...... *G05B 15/02* (2013.01); *A61F 2002/5003* (2013.01); *A61F 2002/503* (2013.01); *A61F 2002/5007* (2013.01); *A61F 2002/5033* (2013.01); *A61F 2002/5072* (2013.01); *A61F 2002/6836* (2013.01); *A61F 2002/701* (2013.01); *A61F 2002/704* (2013.01); *A61F 2002/764* (2013.01); *A61F 2002/7625* (2013.01); *A61F 2002/7635* (2013.01); *A61F 2002/7645* (2013.01)

(56) References Cited

U.S. PATENT DOCUMENTS

| | | | |
|---|---|---|---|
| 4,883,493 A | 11/1989 | Martel et al. | |
| 5,043,929 A | 8/1991 | Kramer et al. | |
| 5,246,465 A | 9/1993 | Rincoe et al. | |
| 5,893,891 A | 4/1999 | Zahedi | |
| 7,153,242 B2 | 12/2006 | Goffer | |
| 7,429,253 B2 | 9/2008 | Shimada et al. | |
| 7,628,766 B1 | 12/2009 | Kazerooni et al. | |
| 7,799,091 B2 | 9/2010 | Herr et al. | |
| 8,057,550 B2 | 11/2011 | Clausen et al. | |
| 8,736,087 B2 | 5/2014 | Mullins et al. | |
| 8,828,093 B1 | 9/2014 | Kuiken et al. | |
| 9,180,025 B2 | 11/2015 | Goldfarb et al. | |
| 2004/0039454 A1 | 2/2004 | Herr et al. | |
| 2004/0049290 A1 | 3/2004 | Bedard | |
| 2004/0054423 A1 | 3/2004 | Martin | |
| 2004/0064195 A1 | 4/2004 | Herr | |
| 2004/0088057 A1 | 5/2004 | Bedard | |
| 2004/0111163 A1 | 6/2004 | Bedard et al. | |
| 2005/0113973 A1 | 5/2005 | Endo et al. | |
| 2006/0173552 A1 | 8/2006 | Roy | |
| 2006/0184280 A1 | 8/2006 | Oddsson et al. | |
| 2006/0224247 A1 | 10/2006 | Clausen et al. | |
| 2006/0249315 A1 | 11/2006 | Herr et al. | |
| 2007/0050044 A1 | 1/2007 | Haynes et al. | |
| 2007/0043449 A1 | 2/2007 | Herr et al. | |
| 2007/0123997 A1 | 5/2007 | Herr et al. | |
| 2009/0192619 A1 | 7/2009 | Martin et al. | |
| 2009/0265018 A1 | 10/2009 | Goldfarb et al. | |
| 2009/0299489 A1 | 12/2009 | Gramnaes | |
| 2009/0326677 A1 | 12/2009 | Phillips et al. | |
| 2010/0094431 A1 | 4/2010 | Albrecht-Laatsch et al. | |
| 2010/0114329 A1 | 5/2010 | Casler et al. | |
| 2011/0112447 A1 | 5/2011 | Hsiao-Wecksler et al. | |
| 2011/0213599 A1 | 9/2011 | Jacobsen et al. | |
| 2011/0224803 A1 | 9/2011 | Goldfarb et al. | |
| 2011/0257764 A1* | 10/2011 | Herr | A61F 2/60 623/24 |
| 2012/0259431 A1* | 10/2012 | Han | A61F 5/0125 623/24 |

OTHER PUBLICATIONS

Sup et al., "Design of a Pneumatically Actuated Transfemoral Prosthesis", IMECE2006-15707, ASME International Mechanical Engineering Congress and Exposition, Nov. 5-10, 2006 by ASME.
iWalk, In the News FAQ: Retrieved on Aug. 12, 2011 from http://iwalk.com/IntheNews/faq.html.
Prosthetics, Hydracadence Knee; Handicap Technologie; Proteor; Retrieved on Aug. 12, 2011 from http://orthopaedics.proteorcom/report.27-hydradence-knee.php.
Power Knee, Instructions for Use; Copyright Ossur 2010.
Novacheck, Tom F. The biomechanics of running. Gait and Posture. vol. 7, 1998. pp. 77-95.
International Search Report and Written Opinion of the International Searching Authority, for International Application No. PCT/US2013/031286, dated Jun. 28, 2013.
European Office Action dated Feb. 10, 2016 for corresponding European Application No. 13713007.6.
McCluney, Christen. Walter Reed Patients Test Next-generation Prosthesis. Dod News. Dec. 10, 2009.

* cited by examiner

US 10,016,290 B2

WALKING CONTROLLER FOR POWERED ANKLE PROSTHESES

CROSS-REFERENCE TO RELATED APPLICATIONS

This application is a § 371 national stage entry of International Application No. PCT/US2013/060110, filed Sep. 17, 2013, which claims priority to and the benefit of U.S. Provisional Application No. 61/701,779 entitled, "DESIGN AND CONTROL METHODOLOGY FOR A POWERED ANKLE/FOOT PROSTHESIS", filed Sep. 17, 2012, both of which are hereby incorporated herein by reference in their entireties.

FIELD OF THE INVENTION

The present invention relates to powered ankle prostheses, and more specifically to apparatus and methods for implementing powered ankle prostheses capable of emulating the biomechanical behaviors associated with the healthy ankle joint.

BACKGROUND

Transtibial amputees typically employ passive dynamic-elastic-response foot/ankle prostheses, which are essentially relatively stiff leaf springs, typically configured with a nominal angle of 90 degrees between the foot and shank. The behavior of the ankle joint in a healthy limb is considerably more varied than the spring-like behavior provided by passive ankle prostheses. In particular, the healthy ankle exhibits a variety of behaviors, including passive behaviors, such as stiffness and/or damping, and active behaviors, such as powered push-off or controlled motion generation. Additionally, these behaviors vary considerably depending on a given activity or type of terrain. For example, when the ankle exhibits a spring-like behavior, the stiffness and equilibrium point of the stiffness will generally vary greatly, depending on the activity and terrain. As such, a passive ankle prosthesis is only able to provide a small subset of the full range of healthy ankle behavior.

Recent advances in battery, microprocessor and motor technologies have made possible the emergence of powered prostheses. An appropriately-designed powered ankle prosthesis is able to emulate the full range of biomechanical behaviors provided by the healthy joint. In order to do so, a prosthesis requires a sensing, actuation, and a transmission system capable of emulating the range of healthy joint impedances observed during locomotion, as well as a control system that recognizes the activity in which the user is currently engaged and provides the appropriate joint behavior accordingly.

Some control strategies for an ankle prosthesis have been described in the engineering literature. Holgate et al. [1] describes a "tibia based controller theory" which essentially seeks to find a continuous relationship between shank angle and ankle angle and a scaling factor based on speed, and a "dynamic pace control", which continuously modulates the ankle period and amplitude based on walking speed. A powered ankle control strategy presented by Au et al. [2] describes first a neural network model and secondly a neuromuscular model, both of which rely on electromyogram (EMG) signal inputs from the amputee's residual limb to position the ankle angle. In another control strategy the phases of gait are decomposed into four parts, and a finite state controller utilizes combinations of linear springs and nonlinear springs, coupled with torque and position sources, respectively, for each portion [3]. An extension of this method has one finite state controller for level ground walking and one for stair climbing, and uses EMG signals from the user to switch between controllers [4]. Finally, [5] presents an approach based on a two state model, one for swing and the other for stance. The swing phase employs position control and the stance phase incorporates a Hill-type muscle model which reacts with a force in proportion to position and speed.

SUMMARY

This patent application describes an embodiment of a powered prosthesis capable of emulating any physical behavior provided by the healthy joint, and additionally describes a control system that utilizes the sensing and actuation system on the prosthesis to provide appropriate ankle joint behaviors. In particular, the control system incorporates a finite-state-based structure, and within each state, emulates the behavior of the healthy joint with strictly passive impedance functions.

DETAILED DESCRIPTION

Figure 1:
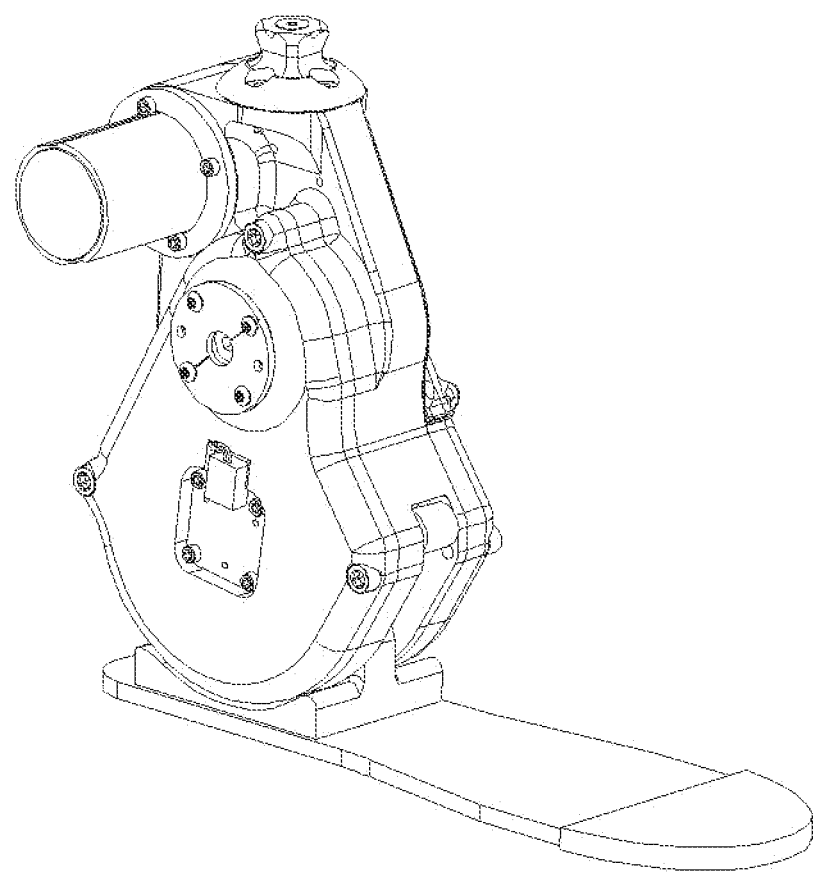
FIG. 1 shows a powered transtibial prosthesis, excluding battery and electronics, in accordance with the various embodiments.

The present invention is described with reference to the attached figures, wherein like reference numerals are used throughout the figures to designate similar or equivalent elements. The figures are not drawn to scale, and they are provided merely to illustrate the instance of the invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The various embodiments are directed to a control methodology that emulates the biomechanical functionality of the healthy ankle with a powered ankle prosthesis, and specifically with a powered ankle prosthesis capable of emulating the impedances produced by the healthy ankle joint. Since the control methodology is dependent upon a prosthesis capable of software-driven emulation of a generalized impedance, design characteristics for suitable prostheses are first described, followed by a description of a specific embodiment of a powered ankle prosthesis capable of such software-driven impedance emulation. Following the design section, a control methodology is described that provides appropriate impedance emulation during walking and other activities.

Prosthesis Design

A. Powered Prosthesis Design Description

A healthy joint is capable of providing a wide range of physical behaviors, as governed by the human neural control system. A passive prosthesis, such as a dynamic-elastic-response ankle, can provide only a small subset of the physical behaviors provided by a healthy joint. In particular, the physical behavior of a spring is generally restricted to energy storage. In mathematical terms, energy storage is characterized by a single-valued, odd algebraic relationship between (joint) torque and angle (i.e., the physical behavior is fundamentally restricted to the first and third quadrants of the torque/angle phase plane). In order to emulate the physical behavior of the healthy joint, a prosthesis must be capable of operating in all quadrants of the torque/angle/angular-velocity phase space. In order to do so, the prosthesis must be capable of power generation. Note, however, that the ability to generate power in the absence of the ability to absorb power does not enable full emulation of healthy joint characteristics. As such, in order to emulate healthy joint behavior, a powered prosthesis must additionally be capable of dynamically absorbing in addition to dynamically generating power. The ability to dynamically absorb power requires either the existence of a low energy path from the output to the actuator, or requires high-fidelity torque sensing at the output of the joint. Further, in order to provide biomechanically useful levels of torque and power, a powered prosthesis should be capable of continuous mechanical power output on the order of 100 W for an average adult ankle, in addition to active joint torque magnitudes on the order of 100 Nm. Thus, a powered prosthesis capable of emulating healthy joint behavior must be able to controllably generate and dissipate biomechanical levels of power at biomechanical magnitudes of torque and at a biomechanically appropriate bandwidth.

Figure 2:
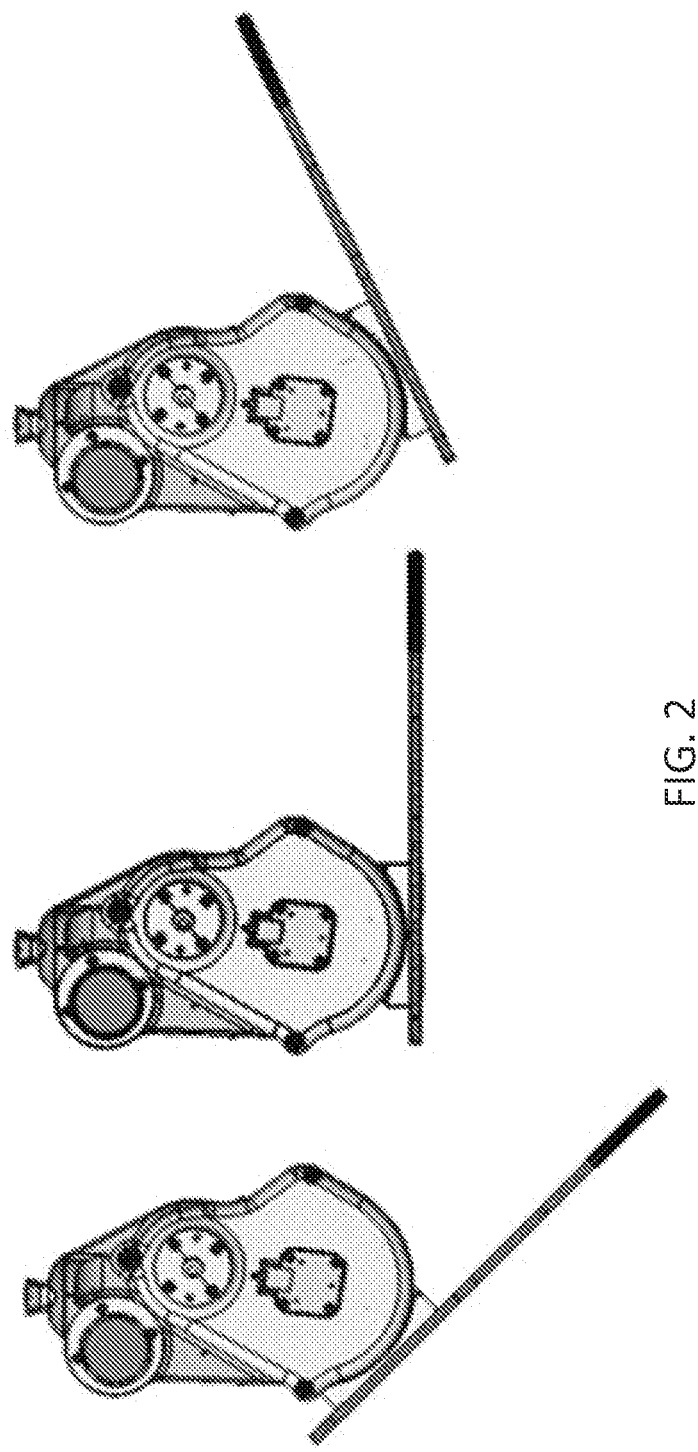
FIG. 2 shows a representation of the range of motion for the powered transtibial prosthesis of FIG. 1.

The general design and operation of a transtibial prosthesis 100 (shown in FIG. 3) that is capable of emulating healthy joint behavior (specifically healthy ankle joint behavior) in accordance with the various embodiments is shown in FIGS. 1 and 2. FIG. 1 shows a photo of the transtibial prosthesis 100, excluding battery and electronics. FIG. 2 shows a representation of the range of motion for the transtibial prosthesis of claim 1. This prosthesis can incorporate an electric motor as the actuator and a series of low-friction belt and chain drives as the transmission, enabling the prosthesis to controllably generate or dissipate biomechanical levels of power. The prosthesis can additionally incorporate joint angle and angular velocity sensing, to enable emulation of passive impedances, such as stiffness and damping, via software-implemented feedback control of angle and angular velocity. The exemplary transtibial prosthesis can have a range of motion of 45 degrees of plantarflexion and 25 degrees of dorsiflexion, as depicted in FIG. 2.

Figure 3:
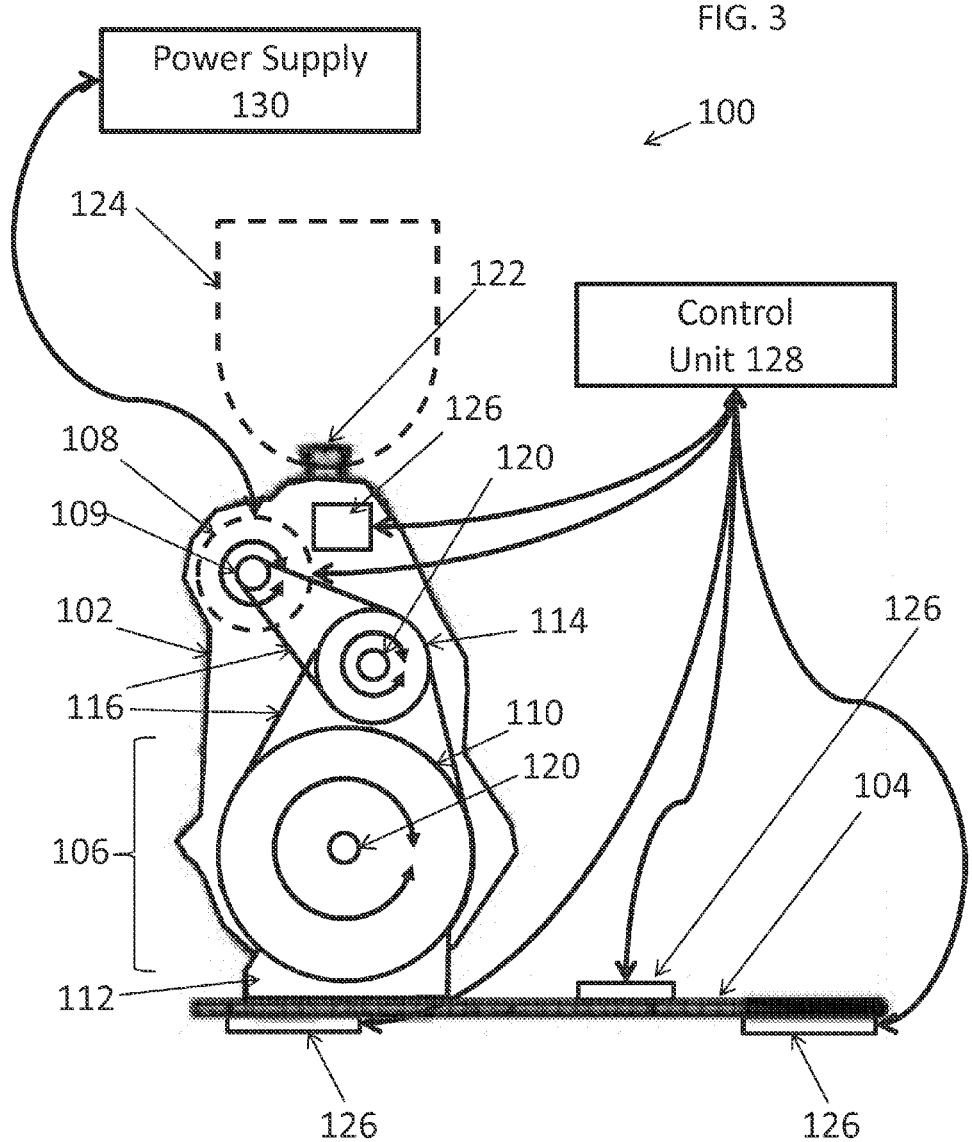
FIG. 3 shows a schematic diagram of the powered transtibial prosthesis.

An exemplary configuration of the various components for a transtibial prosthesis in accordance with the various embodiments is illustrated in FIG. 3. FIG. 3 is a schematic illustration of an exemplary configuration of the components listed above for the transtibial prosthesis 100 of FIG. 1.

As shown in FIG. 3, the transtibial prosthesis 100 (shown in cutaway view in FIG. 3) includes a shank portion 102, a foot portion 104, and an ankle portion 106 to cause the foot portion 104 to move and rotate in space with respect to the shank portion 102. The shank portion 102 consists of a motor 108 configured to cause a rotary stage 110 to rotate, defining a drive train. The foot portion 104 can be mechanically coupled, permanently or removably, to the rotary stage 110 via a mount member 112. In some embodiments, as shown in FIG. 3, the shank portion 102 also serves as a housing for the transtibial prosthesis 100. However, the present disclosure contemplates that a housing separate from the shank portion 102 can also be provided in the various embodiments.

In some embodiments, a drive shaft 109 of the motor 108 can be configured to directly drive the rotary stage 110 to cause motion of foot portion 104. However, in other embodiments, additional drive stages can be used. For example, as shown in FIG. 3, the motor 108 can be coupled to a drive stage 114, which in turn is coupled to the rotary stage 110. The present disclosure contemplates that additional drive stages can be used in the various embodiments. In some embodiments, the motor 108, drive stage 114 (if present), and the rotary stage 110 can be operatively coupled using belts, chains, or other loop elements 116, including a combination of different types of loop elements 116. Based on the configuration of loop elements 116 (e.g., belt or chain), the elements 108, 114, and 110 can be configured as sprockets, pulleys, or any other type of elements compatible with the looped elements 116.

Although FIG. 3 illustrates the use of looped elements 116, the present disclosure also contemplates that the motor 108, drive stage 114 (if present), and the rotary stage 110 can engage with each other directly without the need for looped elements 116. In other example, at least two engaging ones of the drive shaft 109, drive stage 114 (if present), and the rotary stage 110 can be configured as gears or sprockets that engage with each other to effect motion. In another example, the surfaces of least two engaging ones of the drive shaft 109, drive stage 114 (if present), and the rotary stage 110 can have touching surfaces with sufficient friction with each other to effect motion.

Tensioning of the loop elements 116 can be accomplished in a variety of ways. In some embodiments, a tensioning element (not shown) can be provided to place pressure against one or more of the loop elements. In other embodiments, the mounts 118, 120 for the drive stage 114 and the rotary stage 110, respectively, can consist of adjustable mounts. For example, the mounts 118, 120 can be eccentric mounts to allow the positions of the drive stage 114 and the rotary stage 110, respectively, to be adjusted to effect tensioning of the loop elements 116.

In addition to the drive train, the shank portion 102 can also include a connector 122 for connecting the transtibial prosthesis 100 to a socket 124 or a shank portion of a powered or passive prosthesis associated with a user.

The transtibial prosthesis 100 can also include a plurality of sensors 126 communicatively coupled to a control unit 128, which in turn is operatively coupled to the motor 108 to cause the rotation of rotary drive 110 and motion of foot 104. The plurality of sensors 126 can include accelerometer sensors, gyroscopic sensors, load cells, pressure switches, angular position sensors, and angular velocity sensors, to name a few. Such sensors can be utilized to provide signals to the control unit 128 that indicate, for example, ankle joint torque, ankle joint angular velocity, ankle joint angle, acceleration or force along the shank, angular velocity of the shank or foot, shank or foot orientation in space, heel strike, or detect toe push off.

The control unit 128, in turn, can interpret the various signals to cause the motor 108 to operate. A power supply 130 can be provided to supply power for motor 108 to operate.

Figure 4:
FIG. 4 shows a photo of a user wearing a powered transtibial prosthesis configured in accordance with the various embodiments.

In one particular embodiment, the prosthesis mass, including battery and electronics is 2.3 kg. Additionally, such a prosthesis can incorporate a brushless motor, which in conjunction with a 143:1 transmission ratio can generate a maximum ankle joint torque of approximately 70 Nm. A custom embedded system can incorporate a 32-bit microcontroller that runs all control code. The embedded system additionally may include a custom brushless motor servo-amplifier, and an ankle joint angle sensor in addition to a 6-axis inertial measurement unit. The prosthesis may be powered by an on-board lithium-polymer battery (not shown in FIG. 1). Finally the prosthesis may attach to a user's socket via a standard pyramid connector (see FIG. 1). FIG. 4 shows an amputee subject wearing a powered prosthesis in accordance with this embodiment. Note that circuit board is attached to the powered prosthesis in a temporary manner.

Figure 5:
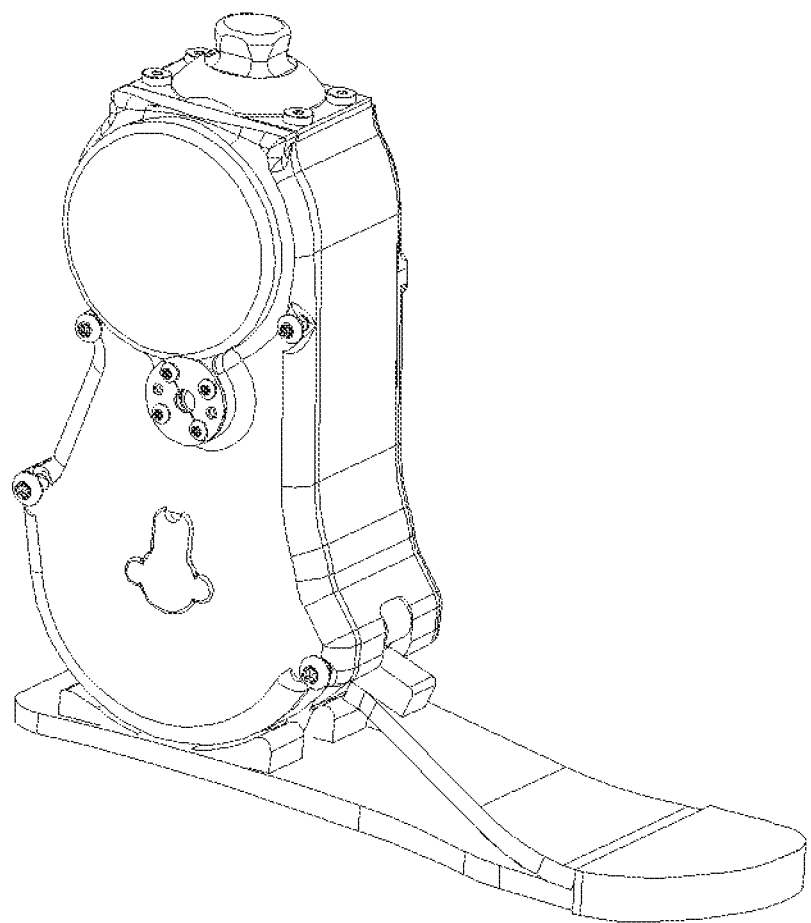
FIG. 5 shows an alternate embodiment of the powered transtibial prosthesis of the various embodiments.

FIG. 5 shows another embodiment of a powered ankle prosthesis with a unidirectional spring element affixed to the foot which enables increased torque and power generation during the push-off phase of walking.

B. Impedance-Based Control Design

Figure 6A:
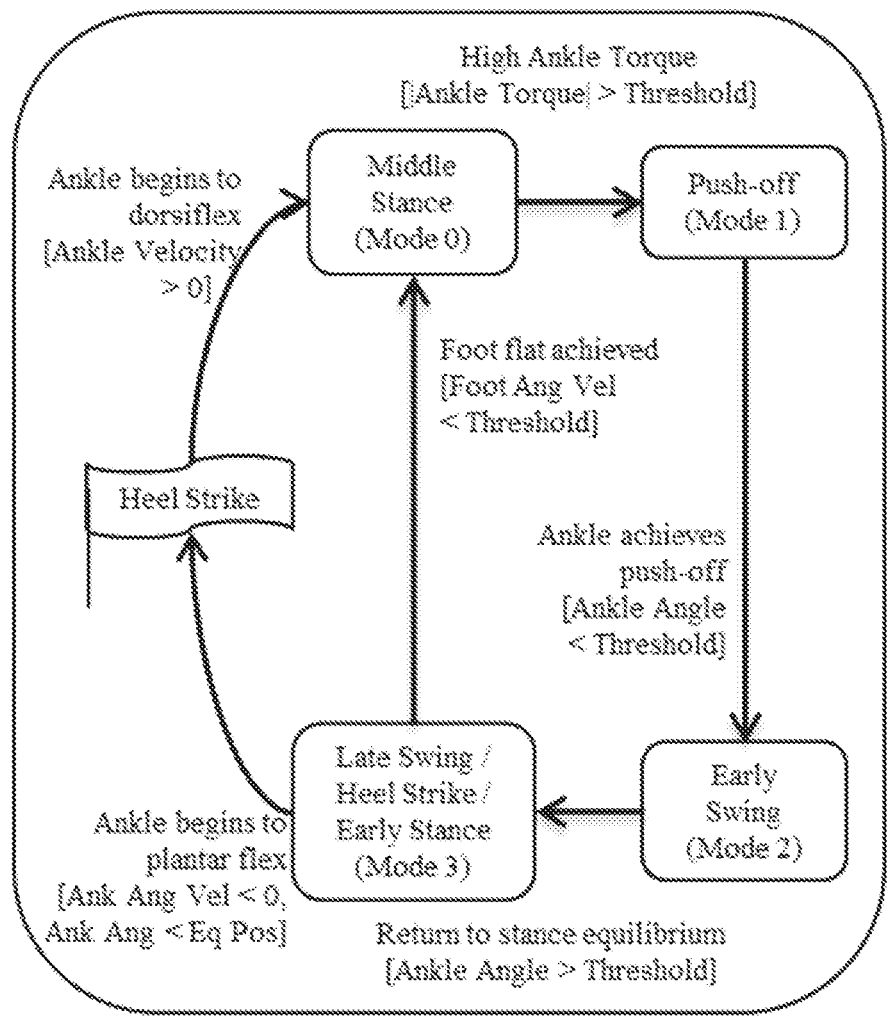
FIG. 6A shows a state chart depicting walking controller gait modes and transitions in accordance with the various embodiments.

The controller of the various embodiments is based on a finite-state-machine structure, although it is unique in the fact that within each state, the prosthesis emulates a passive spring and damper system. FIG. 6A shows a state chart depicting walking controller gait modes and transitions in accordance with the various embodiments. Power may be introduced at the beginning of a given state (or mode) by introducing a new set of impedance parameters (namely, a virtual spring stiffness and equilibrium point and a virtual viscous damping coefficient) which are tuned to interact with the user in such a way that biomechanically normal gait is produced.

In some embodiments, the controller is structured in three levels. The bottom level controls torque at the ankle joint, which is necessary to emulate a desired impedance. The torque reference is generated by the middle level controller, which is implemented as a finite-state machine where each state is defined by passive impedance characteristics for the joint. Specifically, the required joint torque in each state is characterized by a set of impedance parameters corresponding to the following model $$\tau = k_i(\theta - \theta_{ei}) + b_i \omega \qquad (1)$$

where $k_i$, $b_i$, and $\theta_{ei}$ denote linear stiffness, damping coefficient, and equilibrium angle, respectively, for the $i^{th}$ state during a gait cycle. Transitions between gait modes or states are triggered by sensor measurements reaching predetermined thresholds. The top level controller is a supervisory controller which selects an activity mode based on the current activity mode, gait mode, and sensory data comprising the state of the prosthesis. There is a separate middle level controller for each activity which can be selected by the top level controller.

C. Walking Activity Mode Controller

A walking activity mode controller is one such controller which can be selected by the supervisory controller. In one embodiment, ankle behavior during walking is segmented into one of four basic physical behaviors within one cycle of walking gait: viscous damping during heel strike, spring-like support during middle stance, power generation during push-off, and finally a return to a neutral ankle angle during swing. The latter two behaviors are both achieved by emulating spring-like behaviors, each with an appropriate spring stiffness and set point (i.e., a plantarflexed set point for push-off, and a neutral set point for swing). In one embodiment of the controller, heel strike is detected by a sharp peak of acceleration measured along the shank by an accelerometer during the late swing/early stance mode of the controller. In another embodiment of the controller, heel strike is detected by a negative (plantarflexive) ankle angular velocity during late swing/early stance which occurs when the ankle angular position is less than (i.e., more plantarflexed than) the equilibrium position for that mode. During the heel strike/early stance phase of gait (Mode 3), the joint behaves essentially as a damper, plantarflexing to provide shock absorption. Middle stance (Mode 0) may be initiated in a number of ways. In one embodiment of the controller, middle stance (the support phase) may be initiated by heel strike detection followed by ankle dorsiflexion; in another embodiment of the controller, middle stance may be initiated via foot flat detection (foot angular velocity approximately zero, where foot angular velocity is estimated based on ankle angular velocity and shank angular velocity). In another embodiment of the controller, middle stance may be initiated when the angular position of the ankle exceeds a threshold. During middle stance, the ankle behaves largely as a spring with a relatively neutral equilibrium angle. In one embodiment of the controller, the powered prosthesis emulates a nonlinear (stiffening) spring during middle stance. In one embodiment of the controller, push-off (Mode 1) is initiated by exceeding an ankle torque; in another embodiment of the controller, push-off is initiated by exceeding a measurement of shank orientation in space; in another embodiment of the controller, push-off is initiated based on estimated energy transfer for the prosthesis; and in another embodiment of the controller, push-off is initiated based on a combination of these measured and estimated variables. The physical behavior in the push-off mode is achieved by emulating a stiffness with a virtual equilibrium point in a plantarflexed position, at which point a plantarflexive torque is generated at the ankle joint in proportion to the displacement from emulated equilibrium and emulated ankle stiffness. Once push-off has been performed (the ankle reaches a predetermined position threshold), the controller enters early swing (Mode 2), during which the ankle emulates a spring with a neutral equilibrium angle. In one embodiment of the controller, late swing (Mode 3) begins once the ankle has reached the equilibrium angle of the emulated spring; in another embodiment of the controller, late swing begins when the ankle angular velocity becomes positive (ankle is dorsiflexing). In late swing, the controller emulates a light spring at a neutral equilibrium point (i.e., approximately zero degrees), and relatively high damping in preparation for heel strike. This control structure is presented in schematic form in the state chart shown in FIG. 6A. Note that Mode 3 comprises both late swing and heel strike/early stance. Notice also that the heel strike condition in the state chart below is not necessary to enter middle stance (i.e., detection is primarily for the purposes of gait analysis). The gait cycle is therefore essentially separated into 5 segments, wherein the first and last are so similar as to be combined into one state in this embodiment of the controller, but may still be distinguished from one another for classification purposes via heel strike detection.

The impedance parameters for a given gait mode within the walking controller may be modified based on a determination of ground slope or cadence/velocity, in order to emulate the impedance characteristics of the healthy limb during slope ascent and descent, or during changes in walking cadence or speed. In one embodiment of the controller, ground slope is estimated based on the estimated angle of the foot with respect to the horizontal during the middle stance phase when the foot angular velocity is approximately zero. The angle of the foot with respect to the ground is estimated based on the ankle angular position and the orientation of the shank in space. The estimate of ground slope is considerably more precise in the absence of compliance between the ankle joint and the ground, such as in the prosthesis configurations shown in FIGS. 1 and 5. In one embodiment of the controller, the cadence is estimated based on measurement of the duration of the stride and/or the duration of each gait mode within a stride. In another embodiment of the controller, cadence or velocity may be predicted by the ankle angular velocity during the stance phase, or the shank angular velocity during the stance phase.

Figure 6B:
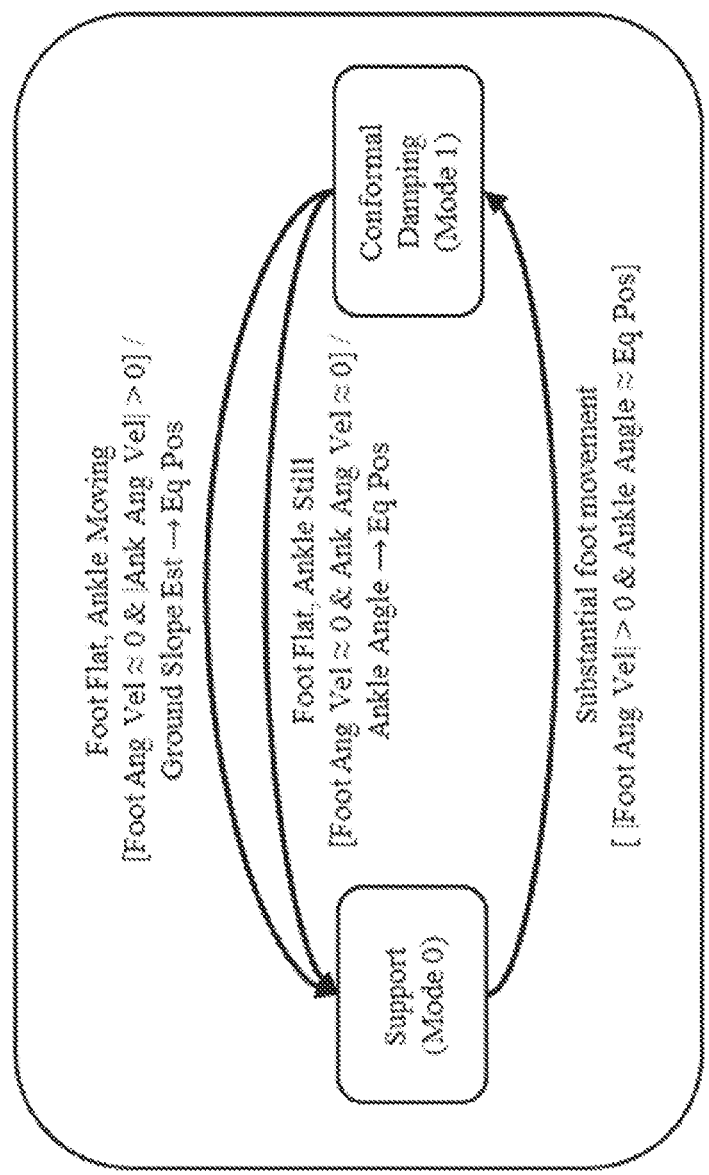
FIG. 6B shows a state chart depicting standing controller gait modes and transitions in accordance with the various embodiments.

Standing is another activity which can be selected by the supervisory controller. One embodiment of a standing controller is depicted in FIG. 6B. In this embodiment, the standing controller comprises a support mode and a conformal (damped) mode. These modes are similar to the middle stance and late swing/early stance modes, respectively, from the walking controller, such that a combined controller which comprises walking and standing may exist in one embodiment of the method. The support mode of the standing controller in one embodiment largely emulates a spring with light damping and is designed for use when the prosthesis is loaded, and the conformal damping mode is designed for use when the device is conforming to the ground. The controller transitions from the support state to the conformal damping state if angular velocity of the foot (estimated by a combination of the ankle angular velocity and the shank angular velocity) is substantial while the ankle angular position is approximately equal to the equilibrium position. The controller may transition from the conformal damping phase to the support phase in multiple ways. If the estimated (sagittal plane) foot angular velocity is approximately zero for a prescribed amount of time while the ankle angular velocity is also approximately zero, the controller will transition to the support mode, setting the virtual spring equilibrium based on the current ankle angular position. If the estimated (sagittal plane) foot angular velocity is approximately zero for some period of time while the ankle angular velocity is substantial, then the controller transitions to the support phase and sets the equilibrium according to the ground slope as estimated by the same method described for the walking controller.

It should be noted that although the various embodiments are described primarily with respect to a transtibial prosthesis, the various embodiments are not limited in this regard. Rather, the various elements of the powered ankle prostheses described can be integrated into prostheses including a knee joint. Alternatively, the design methodology, the control methodology, or both is not limited to prosthetic devices. Rather, these methodologies can also be integrated into orthotic or robotic devices.

EXAMPLES

The following examples and results are presented solely for illustrating the various embodiments and are not intended to limit the various embodiments in any way. The controller described by FIG. 6A was implemented and evaluated on the powered ankle prosthesis shown in FIG. 1. In particular, the biomechanics of the ankle joint during level walking were compared with healthy ankle biomechanics and a passive ankle prosthesis. Additionally, the torque, power, and energy transfer provided by the powered prosthesis were compared to the corresponding information observed in healthy walking.

For the powered prosthesis, the walking controller impedance parameters and transition conditions were determined experimentally in overground walking during a series of training trials, and subsequently on a treadmill at a walking speed of 1.2 m/s (2.7 mph). Specifically, the controller parameters were iteratively tuned based upon a combination of quantitative (ankle joint angle data) and qualitative (user feedback, external observation) information, in order to provide appropriate kinematics and kinetics as well as reliable and natural gait mode transitions.

Ankle joint kinematics for the three cases (healthy, powered, and passive joints) were evaluated via motion capture while walking on a treadmill at similar treadmill speeds. In each of these cases the motion capture was performed with twelve OptiTrack S250e high speed infrared cameras running at 120 Hz using ARENA motion capture software. Thirty-four reflective markers were placed on the subject corresponding to a full skeleton (similar to the Helen Hayes marker set). Note that for the prostheses, the ankle joint marker was placed at the mechanical joint center of the powered prosthesis and at the approximate ankle joint location of the foot shell of the passive prosthesis. The software's skeleton solver was used to track the subject's motion. During the powered prosthesis trials, signals including run time, internal mode, ankle angle, ankle angular velocity, and ankle current were recorded by the prosthesis.

The data collected in ARENA was subsequently processed in MATLAB in order to extract lower limb sagittal joint angles. The joint angles were parsed into single strides (twenty strides per trial) and normalized to a time base of 100%. An offset was manually applied to each ankle for each scenario, such that a neutral ankle position corresponded to a zero joint angle. The mean and standard deviation were computed over all strides for the respective scenarios.

For the powered prosthesis trials, signals recorded from the same 20 strides from each of the two trials were processed to provide joint angles and angular velocities as well as estimated output torques and powers (which were estimated based on measured motor current and known characteristics of the transmission, in addition to measured joint angular velocity). Specifically, the torque and power estimates take into consideration Coulomb friction in the drive train, which was independently measured and characterized. Finally, energy transfer per stride for the powered prosthesis was estimated by numerically integrating the power with respect to run time.

Figure 7A:
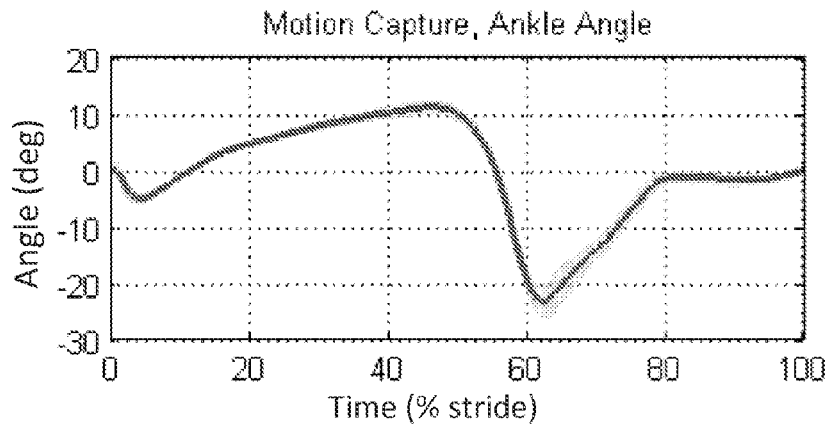
FIG. 7A shows a plot of ankle angle for a healthy subject walking using anatomical ankle joints.
Figure 7B:
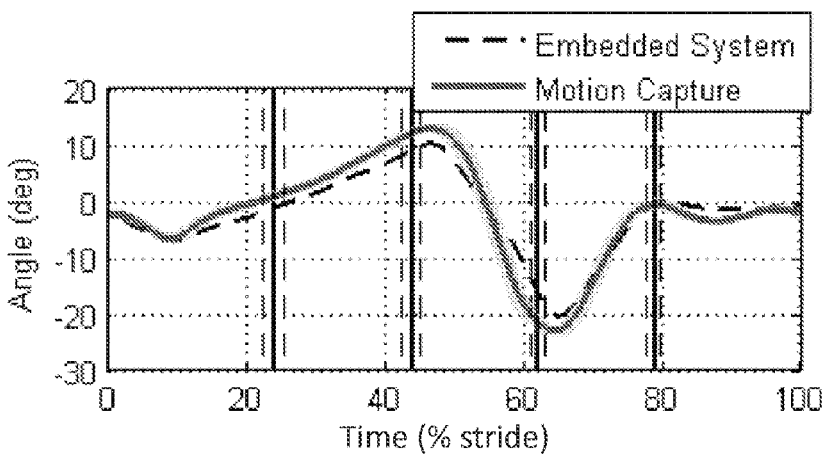
FIG. 7B shows a plot of prosthesis ankle angle when walking with a powered prosthesis in accordance with the various embodiments.
Figure 7C:
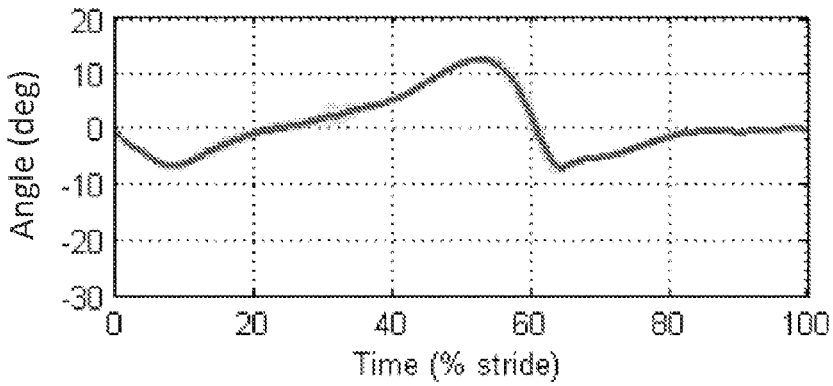
FIG. 7C shows a plot of prosthesis ankle angle when walking with a conventional passive prosthesis.

FIGS. 7A-7C are a set of plots showing the ankle joint angles averaged over 40 strides for healthy walking, the powered prosthesis, and for the passive prosthesis, respectively, all for the same subject. The plot in FIG. 7A shows motion capture data from the healthy subject walking; the plot in FIG. 7B depicts the ankle angle using the powered prosthesis; and the plot in FIG. 7C depicts the trajectory of the passive prosthesis.

It should be noted that the 40 strides represent 20 from each of the two treadmill trials. Also shown on the plots of the powered prosthesis motion capture data are the joint angles as recorded by the prosthesis, in addition to the mean and plus and minus one standard deviation of the gait mode transition stride percentages. Ankle angle trajectory for the healthy joint condition was very similar to that presented in [6].

It should be noted that the passive prosthesis appears to provide similar behavior (a comparable level of stiffness) to the powered prosthesis during middle stance, but does not (and by nature cannot) provide powered push-off. Specifically, unlike the passive prosthesis, the powered prosthesis provides the ankle plantarflexion in late stance that is representative of powered push-off. Evidence that this kinematic feature is reflective of substantial power and energy transfer is indicated in data presented subsequently. Furthermore, note that ankle plantarflexion in late stance in the passive prosthesis occurs substantially later than with both the powered and healthy ankles, suggesting that passive prosthesis reacts to the user removing weight from the prosthesis (likely requiring increased levels of knee and hip torques) rather than actively propelling the user forward.

Comparison between the prosthesis data (for both prostheses) and the healthy subject data during the stance phase of walking suggests that the relationship between torque and position in the healthy subject is nonlinear for this portion of gait. Thus, the ankle stiffness is adjusted during stance to better reflect the nonlinear nature of the healthy ankle. This nonlinearity may better reproduce the stance phase ankle kinematics of the healthy ankle, although it's not clear this difference would be perceived by a user.

Figure 8:
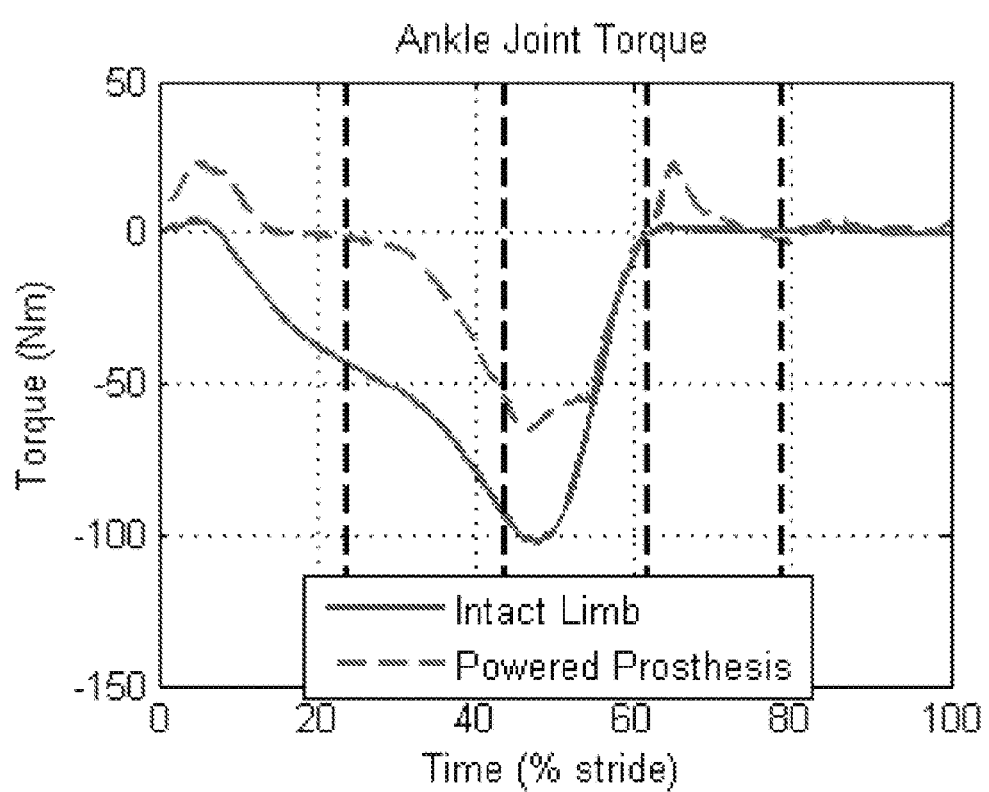
FIG. 8 is a plot depicting ankle joint torque of healthy subjects from the literature and estimated joint torque that would be provided by a powered transtibial prosthesis in accordance with the various embodiments.

FIG. 8 compares joint torques estimated from the powered prosthesis to that of healthy subjects, where the data for the latter was taken from [6] and scaled to the user's body weight. The power curve for healthy subjects was computed by an element-wise multiplication of this torque and the estimated angular velocities of the healthy subject joint; the angular velocity curve was generated using the ankle position data from [6], and deriving stride time from the reported cadence. Note that the disparity in peak torque between the powered prosthesis and intact limb is likely due in part to hardware limitations and limits imposed in the torque controller to protect the motor. Note that the implementation of a unidirectional foot spring in the powered prosthesis, as depicted in FIG. 5, will lower the requisite motor torque during push-off and thus mitigate the aforementioned limitations.

Figure 9:
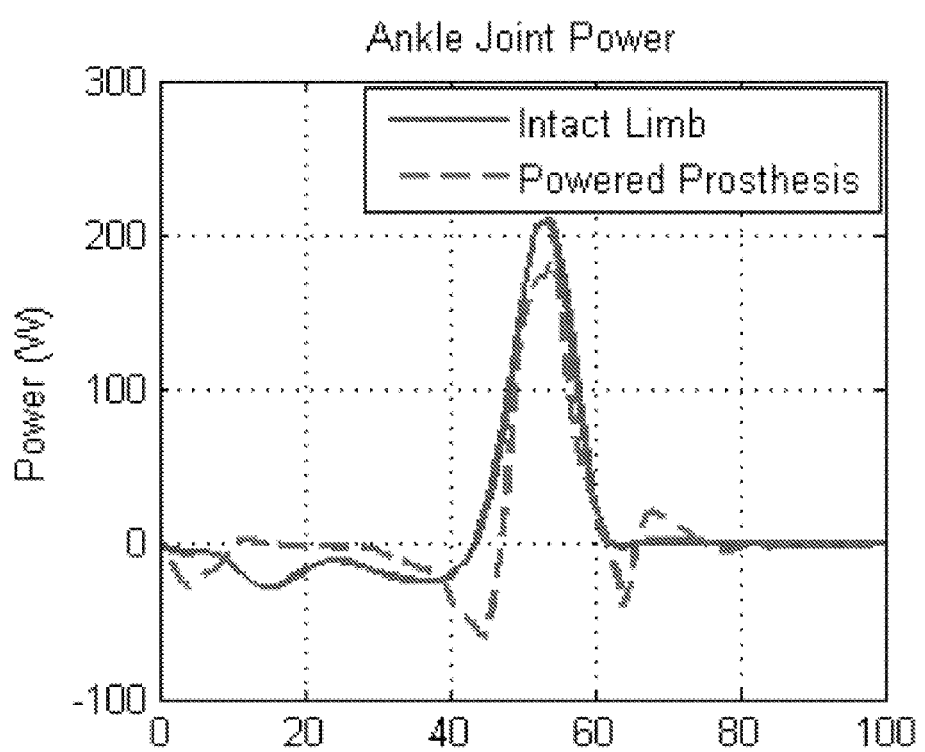
FIG. 9 is a plot depicting ankle joint power of healthy subjects estimated from the literature and estimated joint power provided by a powered transtibial prosthesis in accordance with the various embodiments.

FIG. 9 shows ankle joint power of healthy subjects compared to that of the powered prosthesis. Note that although there are some discrepancies between the two, the powered prosthesis achieves nearly the same peak power as the healthy joint. The controller was also evaluated on its ability to transfer a biomechanically normal level of energy during a gait cycle. By integrating the power generated (and absorbed) by the powered prosthesis with respect to time, the authors estimate that the device transferred approximately 8 joules of energy on average during each stride. A similar method was used to extract average energy transfer for an intact ankle using the estimated power from [6] and estimating the stride time based on cadence. The average energy transfer per stride for the healthy case of walking was thus estimated to be 14.5 joules. Thus the powered prosthesis is clearly transferring significant net energy to the user, although less than that estimated for the healthy ankle. In contrast, however, the passive ankle is able to at most transfer 0 joules to the user, although in practice the energy transfer will be negative (i.e., the passive prosthesis will absorb some net energy from the user).

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

REFERENCES

Each of these documents, referred to by the present disclosure, is hereby incorporated by reference in their entirety:

[1] M. A. Holgate, et al., "Control algorithms for ankle robots: A reflection on the state-of-the-art and presentation of two novel algorithms," in *Biomedical Robotics and Biomechatronics,* 2008. *BioRob* 2008. *2nd IEEE RAS & EMBS International Conference on,* 2008, pp. 97-102.

[2] S. K. Au, et al., "An EMG-position controlled system for an active ankle-foot prosthesis: an initial experimental study," in *Rehabilitation Robotics,* 2005. *ICORR* 2005. *9th International Conference on,* 2005, pp. 375-379.

[3] S. K. Au, et al., "An ankle-foot emulation system for the study of human walking biomechanics," in *Robotics and Automation, 2006. ICRA 2006. Proceedings 2006 IEEE International Conference on,* 2006, pp. 2939-2945.

[4] S. Au, et al., "Powered ankle-foot prosthesis to assist level-ground and stair-descent gaits," *Neural Networks,* vol. 21, pp. 654-666, 2008.

[5] M. F. Eilenberg, et al., "Control of a Powered Ankle-Foot Prosthesis Based on a Neuromuscular Model," *Neural Systems and Rehabilitation Engineering, IEEE Transactions on,* vol. 18, pp. 164173, 2010.

[6] D. A. Winter, *The Biomechanics and Motor Control of Human Gait: Normal, Elderly and Pathological,* 2nd ed. Waterloo, Ontario, Canada: University of Waterloo Press, 1991.

What is claimed is:

1. A method for controlling a powered ankle prosthesis having a shank, a foot, an ankle joint rotatably coupling the shank and the foot, and a motor for directly actuating the ankle joint, comprising operating the motor to cause the ankle joint to be actuated so to have an impedance behavior corresponding to a pre-defined behavior associated with a present state of a series of states of an activity controller for the powered ankle prosthesis, the impedance behavior controlled exclusively via a torque generated by a drive shaft of the motor during operation of the motor;

receiving sensor measurements associated with the powered ankle prosthesis;

based at least on the present state and the sensor measurements, determining to switch from the present state to a different state of the series of states;

wherein within each state, the pre-defined behavior emulates a passive impedance function.

2. The method of claim 1, wherein the passive impedance function is an odd algebraic function that relates the torque at the ankle joint to at least one of an angle or an angular velocity at the ankle joint.

3. The method of claim 1, wherein the activity controller is a walking controller, and wherein the series of states comprising the walking controller comprises at least a stance phase and a swing phase.

4. The method of claim 3, wherein the series of states comprises at least a middle stance state, a push-off state, an early swing state, and a late swing/early stance state, wherein the activity controller in all states is configured to cause the motor to generate the torque so that the emulated behavior is that of a different spring for each state.

5. The method of claim 3, wherein the determination to switch from swing to stance is based on at least a substantial dorsiflexion of the ankle.

6. The method of claim 4, wherein the equilibrium point of each state changes as a function of ground slope.

7. The method of claim 6, wherein the ground slope is estimated by averaging an angle of the foot with respect to an inertial reference frame of the powered ankle prosthesis during a period of time when an angular velocity of the foot with respect to the inertial reference frame is below a predetermined threshold.

8. The method of claim 7, wherein the angle and angular velocity of the foot are calculated using an inertial measurement unit on the shank, in combination with measurement of the angle and angular velocity of the ankle joint.

9. The method of claim 4, wherein the torque is generated in the middle stance state so that the emulated impedance behavior is that of a stiffening spring with a neutral equilibrium point, wherein the torque is generated in the push-off state so that the emulated impedance behavior is that of a high stiffness spring with an equilibrium point at a plantar-flexed position, wherein the torque is generated in the early swing state so that the emulated impedance behavior is that of a spring with the neutral equilibrium point, and wherein the torque is generated in the late swing/early stance state so that the emulated impedance behavior is that of a low stiffness spring with a high damping and the neutral equilibrium point.

10. The method of claim 1, wherein the activity controller is a standing controller, and wherein the series of states comprising the standing controller comprises at least a support state and a conformal state.

11. The method of claim 10, wherein the impedance behavior within the support state is primarily the stiffness behavior, and the impedance behavior within the conformal state is primarily the damping behavior.

12. The method of claim 10, wherein the activity controller switches from the conformal state to the support state when the angular velocity of the foot relative to an inertial reference frame of the powered ankle prosthesis is essentially zero.

13. The method of claim 10, wherein the controller switches from the support state to the conformal state when the angular velocity of the foot relative to an inertial reference frame of the powered ankle prosthesis is substantially nonzero.

14. The method of claim 1, wherein the passive impedance function describes a behavior of a passive spring and damper system having a spring stiffness, an equilibrium point, and a viscous damping coefficient, wherein within each state the spring stiffness, the equilibrium point, and the viscous damping coefficient are pre-defined.

15. A powered ankle prosthesis, comprising:
a shank;
a foot;
an ankle joint rotatably coupling the shank and the foot
one or more sensors configured for generating sensor measurements for the power ankle prosthesis;
an electric motor for actuating the ankle joint;
and
a controller configured for:
operating the motor to cause the ankle joint to be actuated so to have an impedance behavior corresponding to a pre-defined behavior associated with a present state of a series of states of an activity controller for the powered ankle prosthesis, the impedance behavior controlled exclusively via a torque generated by a drive shaft of the motor during operation of the motor;
receiving the sensor measurements;
based at least on the present state and the sensor measurements, determining to switch from the present state to a different state of the series of states
wherein within each state the pre-defined behavior emulates a passive impedance function.

16. The powered ankle prosthesis of claim 15, additionally comprising a unidirectional spring configured to store and release energy during dorsiflexion of the foot.

17. The powered ankle prosthesis of claim 16, wherein the spring is permanently affixed to the foot and mechanically engages and disengages at certain angles.

18. The powered ankle prosthesis of claim 15, further comprising a drive train for transferring the torque between the motor and the ankle joint, wherein the drive train comprises a transmission with multiple stages consisting of at least one of belts or chains.

19. A non-transitory computer-readable storage medium, having stored thereon a computer program for controlling a powered ankle prosthesis having a shank, a foot, an ankle joint rotatably coupling the shank and the foot, and a motor for directly actuating the ankle joint, the computer program comprising a plurality of code sections for carrying out the method comprising:
   operating the motor to cause the ankle joint to be actuated so to have an impedance behavior corresponding to a pre-defined behavior associated with a present state of a series of states of an activity controller for the powered ankle prosthesis, the impedance behavior controlled exclusively via a torque generated by a drive shaft of the motor during operation of the motor;
   receiving sensor measurements associated with the powered ankle prosthesis;
   based at least on the present state and the sensor measurements, determining to switch from the present state to a different state of the series of states;
   wherein within each state the pre-defined behavior emulates a passive impedance function.

20. The computer-readable storage medium of claim 19, wherein the passive impedance function is an odd algebraic function that relates the torque at the ankle joint to at least one of an angle or an angular velocity at the ankle joint.

21. The computer-readable storage medium of claim 19, wherein the activity controller is a walking controller, and wherein the series of states comprising the walking controller comprises at least a stance phase and a swing phase.

22. The computer-readable storage medium of claim 19, wherein the activity controller is a standing controller, and wherein the series of states comprising the standing controller comprises at least a support phase and a conformal phase.

* * * * *